(12) United States Patent
Sato et al.

(10) Patent No.: US 7,163,671 B2
(45) Date of Patent: Jan. 16, 2007

(54) LONG-TERM STABILIZED FORMULATIONS

(75) Inventors: Yasushi Sato, Tokyo (JP); Akihiko Saito, Tokyo (JP); Tadao Yamazaki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 340 days.

(21) Appl. No.: 10/220,523

(22) PCT Filed: Feb. 28, 2001

(86) PCT No.: PCT/JP01/01524

§ 371 (c)(1),
(2), (4) Date: Aug. 28, 2002

(87) PCT Pub. No.: WO01/64241

PCT Pub. Date: Sep. 7, 2001

(65) Prior Publication Data

US 2003/0092622 A1    May 15, 2003

(30) Foreign Application Priority Data

Feb. 29, 2000  (JP) .......................... 2000-053310

(51) Int. Cl.
*A61K 51/00*    (2006.01)
(52) U.S. Cl. ..................................... 424/1.41
(58) Field of Classification Search ............. None
See application file for complete search history.

(56) References Cited

U.S. PATENT DOCUMENTS

| 4,806,524 A | * | 2/1989 | Kawaguchi et al. | ........... 514/8 |
| 6,277,367 B1 | * | 8/2001 | Yamazaki et al. | ......... 424/85.1 |
| 6,908,610 B1 | * | 6/2005 | Sato | ......................... 424/85.1 |

FOREIGN PATENT DOCUMENTS

| EP | 428758 A1 | | 5/1991 |
| EP | 909564 A1 | * | 4/1999 |
| GB | 2193631 A | * | 2/1988 |
| JP | A 154419/81 | | 11/1981 |
| JP | A 63-146829 | * | 6/1988 |
| JP | A 146826/88 | | 6/1988 |
| JP | A 265404/98 | | 10/1988 |
| JP | A 27320/91 | | 2/1991 |
| JP | 2116515 | | 3/1994 |
| JP | A 68137/95 | | 7/1995 |
| JP | 2577744 | | 2/1997 |
| JP | 2000-247903 | | 9/2000 |
| WO | WO 97/40850 | * | 9/2000 |

OTHER PUBLICATIONS

Yu et al., 1984, Journal of Pharmaceutical Sciences, vol. 73, No. 1, pp. 82-86.*
Stedman's Medical Dictionary, 27th Edition, 2000.*
D.S. Jackson 1957, Biochem. J. vol. 65, No. 2, pp. 284-288.*

* cited by examiner

*Primary Examiner*—B. Dell Chism
(74) *Attorney, Agent, or Firm*—Morgan & Finnegan, LLP

(57) ABSTRACT

A stable protein formulation containing tryptophan or a tryptophan derivative or a salt thereof as a stabilizer.

17 Claims, No Drawings

LONG-TERM STABILIZED FORMULATIONS

FIELD OF THE INVENTION

The present invention relates to protein formulations, and particularly to stabilized protein formulations containing tryptophan or a tryptophan derivative or a salt thereof and showing low active ingredient loss even after long-term storage.

PRIOR ART

With the development of genetic recombination technology, various protein formulations have been supplied in stable amounts. To ensure stability, these formulations are supplied in a dosage form of a lyophilized protein ingredient powder to be dissolved just before use in a separately packaged water-soluble diluent, or in the dosage form of a protein solution formulation containing additives for improving stability.

For example, granulocyte colony-stimulating factor (G-CSF), which is a glycoprotein having a molecular weight of about 20,000 and which acts on precursor cells of neutrophils to promote their proliferation and differentiation to maturation, can now be produced in mass in microorganisms or animal cells by genetic engineering techniques. We succeeded in converting the purified G-CSF into formulated products and supplied them to the market as anti-infection agents (Japanese Patent No. 2116515).

G-CSF is used in a very small amount, i.e., a formulation containing 0.1–1000 µg (preferably 5–500 µg) of G-CSF is normally administered once to seven times per week per adult. However, this G-CSF is adsorptive to the walls of ampoules for injection, syringes or the like. Further, G-CSF is unstable and susceptible to extrinsic factors such as temperature, humidity, oxygen, UV rays or the like to undergo physical or chemical changes such as association, polymerization or oxidation, resulting in great loss of activity.

Thus, various dosage designs have been attempted to supply stable G-CSF formulations to the market. For example, formulations containing at least one member selected from the group consisting of (a) at least one amino acid selected from threonine, tryptophan, lysine, hydroxylysine, histidine, arginine, cysteine, cystine and methionine; (b) at least one sulfur-containing reducing agent; or (c) at least one antioxidant have been proposed (Japanese Patent No. 2577744). G-CSF formulations containing a surfactant such as a Polysorbate as a stabilizer were also proposed (JPA No. 146826/88).

Freeze-dried G-CSF formulations containing maltose, raffinose, sucrose, trehalose or an aminosugar were also reported, which are advantageous from the viewpoint of limiting deposits on the container to suppress chemical changes (JPA No. 504784/96).

Some products currently on the market contain a protein such as human serum albumin or purified gelatin used as a stabilizer for suppressing such chemical or physical changes. However, the addition of a protein as a stabilizer involved problems such as the necessity of a very complicated process for removing viral contamination.

However, more G-CSF association products are produced in the absence of such a protein, leading to the problem of deterioration.

Erythropoietin (EPO), which is an acidic glycoprotein promoting differentiation and proliferation of erythroid precursor cells, is also produced in mass by genetic engineering techniques, and we succeeded in converting the purified EPO into formulated products (freeze-dried formulations) and supplied them to the market as drugs for improving renal anemia or the like.

In dosage designs for supplying stable EPO formulations to the market, chemical changes (hydrolysis, disulfide exchange reaction, etc.) or physical changes (denaturation, aggregation, adsorption, etc.) found in EPO should be suppressed. Some products currently on the market contain a protein commonly used as a stabilizer such as human serum albumin or purified gelatin for suppressing such chemical or physical changes. However, the addition of a protein involves the problems described above.

In dosage designs for supplying stable EPO formulations to the market, EPO solution formulations containing an amino acid selected from leucine, tryptophan, serine, glutamic acid, arginine, histidine and lysine and salts thereof as a stabilizer have been proposed (Japanese Patent Application No. 52314/99).

Acetyltryptophan was added to proteins such as albumin, human growth hormones and human B cell differentiation factor (BCDF) (JPB No. 68137/95, JPA No. 265404/98, JPA No. 27320/91). However, it has not been known so far to stabilize hematopoietic factors such as G-CSF or EPO by adding acetyltryptophan.

An object of the present invention is to provide stable protein formulations, which are free from proteins as stabilizers and remain stable even after long-term storage.

DISCLOSURE OF THE INVENTION

As a result of careful studies to achieve the above object, we accomplished the present invention on the basis of the finding that protein formulations can show a high remaining protein level even after long-term storage by adding tryptophan or a tryptophan derivative or a salt thereof as a stabilizer.

Accordingly, the present invention provides a stable protein formulation containing tryptophan or a tryptophan derivative or a salt thereof as a stabilizer.

The present invention also provides said protein formulation wherein the stabilizer is acetyltryptophan or an acetyltryptophan derivative or a salt thereof.

The present invention also provides said protein formulation wherein the stabilizer is acetyltryptophan or a salt thereof.

The present invention also provides said protein formulation wherein the protein has a sugar chain.

The present invention also provides said protein formulation wherein the protein has been produced by genetic recombination.

The present invention also provides said protein formulation wherein the protein has been produced in CHO cells.

The present invention also provides said protein formulation wherein the protein is a hematopoietic factor.

The present invention also provides said protein formulation wherein the protein is erythropoietin.

The present invention also provides said protein formulation wherein the protein is G-CSF.

The present invention also provides said protein formulation, which is substantially free from proteins as stabilizers.

The present invention also provides said protein formulation in the form of a freeze-dried formulation.

The present invention also provides said protein formulation in the form of a solution formulation.

The present invention also provides said protein formulation further containing mannitol.

The present invention also provides said protein formulation further containing a surfactant.

The present invention also provides said protein formulation wherein the surfactant is a polyoxyethylene sorbitan alkyl ester.

The present invention also provides said protein formulation wherein the surfactant is Polysorbate 20 and/or 80.

The present invention also provides said protein formulation having a pH of 4–8.

The present invention also provides said protein formulation having a pH of 6.0–7.5.

The present invention also provides said protein formulation further containing methionine.

The present invention also provides said protein formulation containing 1–100 mM tryptophan or a tryptophan derivative or a salt thereof.

The present invention also provides said G-CSF protein formulation having a remaining protein level of 90% or more after accelerated testing at 50° C. for one month or a remaining protein level of 90% or more after accelerated testing at 60° C. for 2 weeks.

The present invention also provides said EPO protein formulation having a remaining protein level of 85% or more after accelerated testing at 50° C. for one week or after accelerated testing at 60° C. for one week.

THE MOST PREFERRED EMBODIMENTS OF THE INVENTION

Proteins used in formulations of the present invention include, but are not limited to, hematopoietic factors such as granulocyte colony-stimulating factor (G-CSF), granulocyte macrophage colony-stimulating factor (GM-CSF), erythropoietin (EPO) and thrombopoietin; cytokines such as interferon, IL-1 and IL-6; monoclonal antibodies; tissue plasminogen activator (TPA); urokinase; serum albumin; blood coagulation factor VIII; leptin; insulin; and stem cell growth factor (SCF). Preferred proteins are hematopoietic factors such as EPO, G-CSF, GM-CSF or thrombopoietin, more preferably EPO, G-CSF.

Proteins used in formulations of the present invention may be derived from natural sources or preferably obtained by genetic recombination so far as they have substantially the same biological activity as that of physiologically active proteins of mammals, especially human. Gene recombinant proteins may have the same amino acid sequence as that of natural proteins or may contain deletion, substitution or addition of one or more amino acids in said amino acid sequence while maintaining said biological activity. Proteins may also be chemically modified with PEG or the like.

Proteins used as active ingredients in the present invention include, for example, proteins having a sugar chain. The sugar chain may be derived from any source, but preferably those added to mammalian cells. Mammalian cells include, for example, Chinese hamster ovary (CHO) cells, BHK cells, COS cells, human-derived cells, etc., among which CHO cells are most preferred.

When the protein used in protein formulations of the present invention is G-CSF, any high-purity G-CSF can be used. G-CSF in the present invention may be prepared by any process, e.g., they may be extracted from cultures of a human tumor cell line and isolated and purified by various techniques or may be produced by genetic engineering techniques in bacterial cells such as E. coli; yeast cells; animal culture cells such as Chinese hamster ovary (CHO), C127 or COS cells and then extracted and isolated and purified by various techniques. G-CSF is preferably produced by genetic recombination in E. coli, yeast or CHO cells, most preferably by genetic recombination in CHO cells. G-CSF chemically modified with PEG or the like is also included (see International Publication WO90/12874).

When the protein used in protein formulations of the present invention is EPO, EPO may be prepared by any process, e.g. it may be extracted from human urine and isolated and purified by various techniques or may be produced by genetic engineering techniques (see JPA No. 12288/86, for example) in Chinese hamster ovary (CHO) cells, BHK cells, COS cells, human-derived cells or the like and then extracted and isolated and purified by various techniques. EPO chemically modified with PEG or the like is also included (see International Publication WO90/12874). EPO having no sugar chain and chemically modified with PEG or the like is also included. EPO analogs are also included, in which EPO has been modified to increase the number of one or more glycosylation sites at the N-linked carbohydrate chain binding site or O-linked carbohydrate binding site in the amino acid sequence of EPO (see JPA No. 151398/96 and JPA No. 506023/96, for example). Moreover, the amount of sugar chains may be increased by increasing the content of sialic acid or the like without changing the number of sugar chain-binding sites.

Preferably, protein formulations of the present invention are substantially free from proteins such as human serum albumin or purified gelatin as stabilizers.

When the protein is G-CSF, for example, the protein formulation of the present invention has a remaining protein level of 90% or more, preferably 95% or more after accelerated testing at 50° C. for one month or a remaining protein level of 90% or more, preferably 95% or more after accelerated testing at 60° C. for 2 weeks. When the protein is EPO, the protein formulation of the present invention has a remaining protein level of 85% or more after accelerated testing at 50° C. for one week or after accelerated testing at 60° C. for one week. Therefore, they are very stable as compared with previously known protein formulations.

Protein formulations of the present invention have a pH of 4–8, preferably 6.0–7.5. However, these values are non-limitative but the pH depends on the protein contained. For example, G-CSF formulations preferably have a pH of 5–7, more preferably 6.0–6.7, still more preferably 6.5. EPO formulations preferably have a pH of 5–8, more preferably 5.5–7.0.

The amount of proteins contained in protein formulations of the present invention can be determined depending on the proteins used, the type of disease to be treated, the severity of the patient, the age of the patient and other factors. Generally, proteins are contained in an amount of 0.01 µg/ml or more, preferably 0.1 µg/ml or more, more preferably 1 µg/ml or more, still more preferably 10 µg/ml or more, most preferably 50 µg/ml or more. For example, EPO is normally contained in an amount of 100–500,000 IU/ml, preferably 200–100,000 IU/ml, more preferably 750–72,000 IU/ml. G-CSF is normally contained in an amount of 1–1000 µg/ml, preferably 10–800 µg/ml, more preferably 50–500 µg/ml.

Tryptophan or tryptophan derivatives or salts thereof used in the present invention include free tryptophan or tryptophan derivatives and salts thereof such as sodium salts, potassium salts and hydrochlorides. Tryptophan or tryptophan derivatives or salts thereof used in formulations of the present invention may be D-, L- and DL-isomers, more preferably L-isomers. Tryptophan derivatives include tryptophan methyl ester hydrochloride, tryptophanol, methyl tryptophan, benzyloxytryptophan, bromotryptophan, fluorotryptophan, hydroxytryptophan, hydroxytryptophan ethyl ester hydrochloride, hydroxytryptophan hydrate, methoxytryptophan, acetyltryptophan, acetyltryptophan ethyl ester, acetyltryptophan amide, oleyltryptophan ethyl ester, tryptophan butyl ester hydrochloride, tryptophan ethyl ester hydrochloride, tryptophan methyl ester hydrochloride, tryptophan octyl ester hydrochloride, tryptophan amide hydrochloride, fluorotryptophan, tryptophanol oxalate, azatryptophan hydrate, fluorenylmethoxycarbonyltryptophan, carbobenzyloxytryptophan, butoxycarbonyltryptophan, methoxycarbonyltryptophan methyl ester, tryptophan naphthyl amide, carbobenzyloxytryptophan, carbobenzyloxyalanyl tryptophan, carbobenzyloxyisoleucyl tryptophan, carbobenzyloxyisoleucyl tryptophan methyl ester, carbobenzyloxymethionyl tryptophan, carbobenzyloxymethionyl tryptophan amide, carbobenzyloxynorleucyl tryptophan methyl ester, carbobenzyloxynorvalyl tryptophan, carbobenzyloxyphenylalanyl tryptophan amide, carbobenzyloxytryptophan amide, carbobenbyloxytyrosyl tryptophan amide, carbobenzyloxyglycyl tryptophan, carbobenzyloxyglycyl tryptophan methyl ester, carbobenzyloxyglycyl tryptophan amide, carbobenzyloxyglycyl glycyl tryptophan methyl ester, carbobenzyloxymethionyl tryptophan methyl ester, carbobenzyloxynorvalyl tryptophan methyl ester, carbobenzyloxynorvalyl tryptophan amide, carbobenzyloxyphenylalanyl tryptophan methyl ester, carbobenzyloxysarcosyl tryptophan methyl ester, carbobenzyloxysarcosyl tryptophan amide, carbobenzyloxytryptophan naphthyl amide, carbobenzyloxytryptophyl tryptophan methyl ester, chloroacetyltryptophan, dansyltryptophan chlorohexyl ammonium, glycyl tryptophan, homotryptophan hydrochloride, alanyl tryptophan, acetyltryptophan methyl ester, carbobenzyloxytryptophan nitrophenyl ester, furylacryloyl tryptophan amide, carbamyl tryptophan, chloroacetyltryptophan, nitrophenylsulfenyl tryptophan diammonium, acetyltryptophan propyl ester, etc. In the present invention, acetyltryptophan and acetyltryptophan derivatives are especially preferred. Acetyltryptophan derivatives include acetyltryptophan methyl ester, acetyltryptophan ethyl ester, acetyltryptophan propyl ester, acetyltryptophan amide, chloroacetyltryptophan, etc.

The amount of tryptophan or tryptophan derivatives or salts thereof added to formulations of the present invention depends on the nature and concentration of the proteins used, dosage form (freeze-dried formulations or solution formulations) and the derivatives used. They are typically contained in freeze-dried formulations at a final dose of 0.1–300 mM, preferably 1–200 mM, more preferably 1–100 mM. They are typically contained in solution formulations at a final dose of 0.1–30 mM, preferably 0.5–20 mM, more preferably 0.5–10 mM. In the case of freeze-dried formulations, stable protein formulations with excellent resolubility can be provided at 0.1–30 mM, preferably 1–30 mM, more preferably 1–10 mM.

The weight ratio of proteins and acetyltryptophan in freeze-dried formulations is generally 1:1–1:1000. In the case of EPO, it is preferably 1:1–1:500, more preferably 1:2–1:300. In the case of G-CSF, it is preferably 1:1–1:500, more preferably 1:10–1:300. In solution formulations, it is generally 1:1–1:1000, and in the case of EPO, it is preferably 1:1–1:500, more preferably 1:10–1:250, still more preferably 1:100–1:150, most preferably 1:120.

Formulations of the present invention preferably contain methionine. It was observed that the production ratio of G-CSF oxidized at methionine residues can be kept below detection limit by adding methionine (Japanese Patent Application No. 52314/99). Without wishing to be bound to any specific theory, we assume that the added methionine is oxidized in place of methionine residues of G-CSF with the result that the production ratio of G-CSF oxidized at methionine residues decreases.

Formulations of the present invention may contain isotonizing agents, e.g., polyethylene glycol; and sugars such as dextran, mannitol, sorbitol, inositol, glucose, fructose, lactose, xylose, mannose, maltose, sucrose and raffinose. Mannitol is especially preferred. The amount of mannitol added into formulations is 0.1–10%, more preferably 0.5–6%.

Formulations of the present invention may further contain surfactants. Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6–18;

anionic surfactants, e.g., alkyl sulfates having a C10–18 alkyl group such as sodium cetyl sulfate, sodium lauryl sulfate, sodium oleyl sulfate; polyoxyethylene alkyl ether sulfates having an average EO mole number of 2–4 and a C10–18 alkyl group such as sodium polyoxyethylene lauryl sulfate; alkyl sulfosuccinic acid ester salts having a C8–18 alkyl group such as sodium laurylsulfosuccinate; and natural surfactants, e.g., lecithin; glycerophospholipids; sphingophospholipids such as sphingomyelin; sucrose fatty acid esters of C12–18 fatty acids. One or more of these surfactants may be added in combination to formulations of the present invention.

Preferred surfactants are polyoxyethylene sorbitan fatty acid esters, more preferably Polysorbates 20, 21, 40, 60, 65, 80, 81, 85, most preferably Polysorbates 20 and 80.

The amount of surfactants to be added to protein formulations of the present invention is typically 0.0001–10% (w/v), preferably 0.001–5%, more preferably 0.005–3%. Protein formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added may also be contained, e.g., inorganic salts such as sodium chloride, potassium chloride, calcium chloride, sodium phosphate, potassium phosphate, sodium bicarbonate; and organic salts such as sodium citrate, potassium citrate, sodium acetate.

Protein formulations of the present invention include solution formulations, freeze-dried formulations, spray-dried formulations, etc. Freeze-dried formulations are most preferred.

Formulations of the present invention can be prepared by dissolving these components in an aqueous buffer known in the art of solution formulations such as phosphate buffers (preferably sodium monohydrogen phosphate—sodium dihydrogen phosphate system) and/or citrate buffers (preferably sodium citrate buffer) to prepare a solution formulation, or freeze-drying or spray-drying thus prepared solution formulation by standard procedures.

Stabilized protein formulations of the present invention are normally administered via parenteral routes such as injection (subcutaneous, intravenous or intramuscular injection) or percutaneous, mucosal, nasal or pulmonary administration, but may also be orally administered.

Protein formulations of the present invention are normally packed in a sealed and sterilized plastic or glass container, and dissolved in pure water (sterilized water for injection) before use.

When the protein is G-CSF, protein formulations of the present invention show a very good remaining G-CSF level even after accelerated testing at 50° C. for 1 month or accelerated testing at 60° C. for 2 weeks as demonstrated in the examples below. G-CSF formulations of the present invention show a remaining G-CSF level of 90% or more, preferably 95% or more after accelerated testing at 50° C. for 1 month, or a remaining G-CSF level of 90% or more, preferably 95% or more after accelerated testing at 60° C. for 2 weeks.

When the protein is EPO, protein formulations of the present invention containing acetyltryptophan even in a very small amount showed a very good remaining EPO level of 5% or more as compared with acetyltryptophan-free groups after accelerated testing at 50° C. for 1 week or accelerated testing at 60° C. for 1 week. EPO formulations of the present invention show a remaining EPO level of 85% or more after accelerated testing at 50° C. for 1 week or accelerated testing at 60° C. for 1 week.

The weight ratios of the G-CSF or EPO and acetyltryptophan used in the examples below and the remaining protein levels after accelerated testing using them are shown in Table 1. The weight ratios and remaining levels shown here are merely examples of the present invention without, however, limiting the scope of the present invention thereto.

TABLE 1

| Protein level | Acetyl-tryptophan level | Weight ratio | 60° C., 1 week | 60° C., 2 weeks | 50° C., 1 month |
|---|---|---|---|---|---|
| Freeze-dried formulations | | | | | |
| G-CSF 100 µg/mL | 60 mM | 1:150 | — | 99.9% | 100.4% |
| EPO 8.3 µg/mL (1500 IU/mL) | 4 mM (1 mg/mL) | 1:120 | 88.9% | — | — |
| EPO 8.3 µg/mL (1500 IU/mL) | 8 mM (2 mg/mL) | 1:240 | 89.8% | — | — |
| EPO 267 µg/mL (48000 IU/mL) | 4 mM (1 mg/mL) | 1:4 | 95.7% | | |
| Solution formulation | | | | | |
| EPO 8.3 µg/mL (1500 IU/mL) | 4 mM | 1:120 | 85.2% (50° C., 1 week) | | |

When formulations of the present invention are G-CSF formulations, they are clinically very useful as they were found to improve protective functions based on immune response such as resistance of the patient or activity when they were coadministered with drugs such as antibiotics, antibacterial agents or anticancer agents in the chemotherapy of infectious diseases or cancer. Therefore, formulations of the present invention can be administered in combination with these drugs.

The results of the examples below show that formulations of the present invention can increase the remaining G-CSF or EPO level after long-term storage especially at normal temperatures by adding tryptophan or a tryptophan derivative.

INDUSTRIAL APPLICABILITY

Protein formulations of the present invention are stable formulations showing a very high remaining protein level even after long-term storage.

The following examples further illustrate the present invention without, however, limiting the same thereto. Various changes and modifications can be made by those skilled in the art on the basis of the description of the invention, and such changes and modifications are also included in the present invention.

EXAMPLES (1) Test Method and Assay Method for G-CSF Formulations

Test Method

Formulated solutions containing G-CSF were prepared and aseptically filtered, and then precisely 1 mL each was aseptically packed in a vial and freeze-dried. After completion of freeze-drying, the vial was completely capped to prepare G-CSF freeze-dried formulations. The G-CSF used was a recombinant G-CSF and all the amino acids added were free L-isomers.

Thus aseptically prepared G-CSF-containing freeze-dried formulations were allowed to stand in an incubator at 60° C. for 2 weeks or in an incubator at 50° C. for 1 month.

Accelerated and unaccelerated formulations were dissolved in 1 mL of pure water to prepare test samples for the assay below.

Assay Method

The G-CSF content was assayed by reverse phase high-speed liquid chromatography using a C4 reverse phase column (4.6 mm×250 mm, 300 angstroms) with a mobile phase consisting of pure water, acetonitrile and trifluoroacetic acid. The amount equivalent to 5 μg of G-CSF was injected and G-CSF was eluted with an acetonitrile gradient and spectroscopically detected at a wavelength of 215 nm.

The G-CSF content determined by this method was used to calculate the remaining level (%) according to the following equation after acceleration at 60° C. for 2 weeks and 50° C. for 1 month.

$$\text{Remaining level (\%)} = \frac{\left(\begin{array}{c}\text{G-CSF content after acceleration} \\ \text{for a given period}\end{array}\right)}{\left(\begin{array}{c}\text{G-CSF content in unaccelerated} \\ \text{formulation}\end{array}\right)} \times 100$$

(2) Test Method and Assay Method for EPO Formulations

Test Method

Formulated solutions containing EPO were prepared and aseptically filtered, and then precisely 0.5 mL each was aseptically packed in a vial to prepare solution formulations. Thus prepared solution formulations were freeze-dried. After completion of freeze-drying, the vial was completely capped to prepare EPO freeze-dried formulations. The EPO used was a recombinant EPO obtained from CHO cells and the acetyltryptophan added was a free L-isomer.

Thus aseptically prepared EPO-containing freeze-dried formulations were allowed to stand in an incubator at 50° C. for 1 week or in an incubator at 60° C. for 1 week.

Assay Method

The EPO content was assayed by reverse phase high-speed liquid chromatography using a VyDAC 214TP54 column with a mobile phase consisting of a two-part mixed gradient of water/acetonitrile/trifluoroacetic acid. The content was spectroscopically detected at a wavelength of 214 nm.

Example 1

Effect of Various Amino Acids on the Remaining G-CSF Level

G-CSF freeze-dried formulations having the following composition:

| | |
|---|---|
| G-CSF | 100 μg/mL |
| Amino acid | 60 mM |
| Mannitol | 2.5% |
| Polysorbate 20 | 0.01% | were prepared and allowed to stand in an incubator at 60° C. for 2 weeks or in an incubator at 50° C. for 1 month, and then assayed for the remaining level (%) according to the test method described above. The results are shown in Table 2 below.

TABLE 2

| Amino acid added | 60° C., 2 weeks | 50° C., 1 month |
|---|---|---|
| Glycine | 82.3 | 86.4 |
| Alanine | 79.1 | 87.2 |
| Valine | 82.7 | 89.5 |
| Leucine | 74.8 | 81.7 |
| Isoleucine | 78.7 | 79.4 |
| Serine | 81.6 | 88.0 |
| Threonine | 81.3 | 87.7 |
| Arginine | 77.2 | 93.7 |
| Methionine | 72.7 | 78.0 |
| Aspartic acid | 82.8 | 87.4 |
| Glutamic acid | 75.1 | 86.7 |
| Asparagine | 84.2 | 87.5 |
| Glutamine | 83.0 | 86.9 |
| Lysine | 77.7 | 90.4 |
| Phenylalanine | 82.4 | 89.4 |
| Tryptophan | 94.0 | 94.0 |
| Histidine | 81.5 | 93.1 |
| Proline | 58.2 | 81.3 |

The formulation containing tryptophan showed excellent remaining levels after standing in an incubator at 60° C. for 2 weeks as well as in an incubator at 50° C. for 1 month.

Example 2

Effect of Acetyltryptophan Levels on the Remaining G-CSF Level

The results of samples 1–4 containing 100 μg/mL G-CSF, 6 mM methionine, 5% mannitol, 0.01% Polysorbate 20 and varying amounts of acetyltryptophan are shown in Table 3 below. Acetyltryptophan was used as a solution in an NaOH solution.

TABLE 3

| | Sample 9 | Sample 10 | Sample 11 | Sample 12 |
|---|---|---|---|---|
| G-CSF | 100 μg/mL | 100 μg/mL | 100 μg/mL | 100 μg/mL |
| Acetyl-tryptophan | 0 | 30 mM | 60 mM | 90 mM |
| 50° C., 1 month | 78.2% | 99.2% | 100.4% | 100.1% |
| 60° C., 2 weeks | 72.1% | 95.0% | 99.9% | 100.1% |

Marked remaining levels were observed at any acetyltryptophan levels of 30 mM, 60 mM and 90 mM.

Example 3

Effect of the Addition of Acetyltryptophan on the Remaining EPO Level

Preparation of EPO Solution Formulations

Solution formulations containing the following components per ml of the formulated solutions were prepared and adjusted to pH 7.0 with 10 mM phosphate buffer.

| | |
|---|---|
| EPO | 1500 IU (or 48000 IU) |
| Mannitol | 50 mg |
| Polysorbate 80 | 0.05 mg |
| Acetyltryptophan | 4 mM (or 8 mM) |

Freeze-dried formulations were prepared from the above solution formulations.

(1) Remaining levels in solution formulations

The remaining EPO levels in the solution formulations after standing at 50° C. for 1 week are shown in Table 4.

TABLE 4

|  | Sample 13 | Sample 14 |
|---|---|---|
| EPO [μg/mL] | 8.3 | 8.3 |
| Acetyltryptophan [mM] | 0 | 4 |
| Remaining level after storage at 50° C., 1 week (%) | 79.0 | 85.2 |

(2) Remaining levels in freeze-dried formulations

The remaining EPO levels in the freeze-dried formulations after standing at 60° C. for 1 week are shown in Table 5.

TABLE 5

|  | Sample 13 | Sample 14 | Sample 15 | Sample 16 | Sample 17 |
|---|---|---|---|---|---|
| EPO [μg/mL] | 8.3 | 8.3 | 8.3 | 267 | 267 |
| Acetyltryptophan [mM] | 0 | 4 | 8 | 0 | 4 |
| Remaining level after storage at 60° C., 1 week (%) | 79.7 | 88.9 | 89.8 | 88.4 | 95.7 |

Samples 14, 15 and 17 showed very good resolubility.

The invention claimed is:

1. A stable protein formulation containing acetyltryptophan or a salt thereof as a stabilizer, wherein the protein is a hematopoietic factor, and wherein said formulation is free from proteins as stabilizers.

2. The protein formulation of claim 1 wherein the protein is erythropoietin.

3. The protein formulation of claim 1 wherein the protein is granulocyte colony-stimulating factor (G-CSF).

4. The protein formulation of claim 1 wherein the protein has been produced by genetic recombination.

5. The protein formulation of claim 2 wherein the protein has been produced in CHO cells.

6. The protein formulation of claim 1 in the form of a freeze-dried formulation.

7. The protein formulation of claim 1 in the form of a solution formulation.

8. The protein formulation of claim 1 further containing mannitol.

9. The protein formulation of claim 1 further containing a surfactant.

10. The protein formulation of claim 9 wherein the surfactant is a polyoxyethylene sorbitan alkyl ester.

11. The protein formulation of claim 10 wherein the surfactant is Polysorbate 20 and/or 80.

12. The protein formulation of claim 1 having a pH of 4–8.

13. The protein formulation of claim 12 having a pH of 6.0–7.5.

14. The protein formulation of claim 1 further containing methionine.

15. The protein formulation of claim 1 containing 1–100 mM acetyltryptophan or a salt thereof.

16. The protein formulation of claim 1 having a remaining protein level of 90% or more after accelerated testing at 50° C. for one month or a remaining protein level of 90% or more after accelerated testing at 60° C. for 2 weeks.

17. The protein formulation of claim 1 having a remaining protein level of 85% or more after accelerated testing at 50° C. for one week or after accelerated testing at 60° C. for one week.

* * * * *